United States Patent [19]
Groezinger

[11] Patent Number: 6,101,407
[45] Date of Patent: Aug. 8, 2000

[54] METHOD AND SYSTEM FOR REMOTELY VIEWING AND CONFIGURING OUTPUT FROM A MEDICAL IMAGING DEVICE

[75] Inventor: John L. Groezinger, Cottage Grove, Minn.

[73] Assignee: Eastman Kodak Company, Rochester, N.Y.

[21] Appl. No.: 09/023,551

[22] Filed: Feb. 13, 1998

[51] Int. Cl.[7] .............................. A61B 5/00; A61B 8/00
[52] U.S. Cl. ..................... 600/407; 600/437; 128/922
[58] Field of Search .................... 600/407, 425, 600/300, 437; 705/3; 128/922

[56] References Cited

U.S. PATENT DOCUMENTS

| | | | |
|---|---|---|---|
| 5,321,520 | 6/1994 | Inga et al. | 358/403 |
| 5,715,823 | 2/1998 | Wood et al. | 128/904 |
| 5,853,367 | 12/1998 | Chalek et al. | 600/437 |
| 5,857,967 | 1/1999 | Frid et al. | 600/301 |
| 5,891,035 | 4/1999 | Wood et al. | 600/437 |
| 5,936,539 | 8/1999 | Fuchs | 128/903 X |
| 5,997,488 | 12/1999 | Jackson | 600/437 |

FOREIGN PATENT DOCUMENTS

WO 96/16380   5/1996   WIPO .

OTHER PUBLICATIONS

Li et al., "A World Wide Web Telemedicine System," Medical Imaging 1996; PACS Design and Evaluation: Engineering and Clinical Issues, Newport Beach, CA, *Proceedings of the SPIE —The International Society for Optical Engineering*, 1996, (Feb. 13–15, 1996) vol. 2711, pp. 427–439.

Wolf et al., "WebVideo —Interactive Video in the World Wide Web," Proceedings JENC7, (7th Joint European Networking Conference), Networking in the Information Society, Budapest, Hungary (May 13–16, 1996) pp. 113–1 to 113–7.

*Primary Examiner*—Francis J. Jaworski
*Attorney, Agent, or Firm*—William F. Noval

[57] ABSTRACT

A method and system for remotely viewing and configuring output from a medical imager is described. A medical imager having an embedded web server generates an HTML document according to medical images received from various medical modalities. Imaging information is communicated in the HTML document to allow a remote machine to manipulate the images and display the images in a manner that accurately represents their printed output by the imager. The invention thus provides accurate viewing of the medical images from a remote machine and facilitates remote configuration of the medical imager. Other advantages include the ability to easily select conversion mechanisms best suited for specific requirements of the hospital's medical modalities without traveling to the hospital and burdening medical staff. The present invention also allows for remote monitoring of operation statistics such as usage of imaging media and other supplies.

20 Claims, 2 Drawing Sheets

METHOD AND SYSTEM FOR REMOTELY VIEWING AND CONFIGURING OUTPUT FROM A MEDICAL IMAGING DEVICE

FIELD OF THE INVENTION

This invention relates generally to the field of remote diagnostics including remote maintenance and configuration of a medical imaging device. More particularly, the invention is directed to a method and system for remotely viewing and configuring output from a medical imaging device.

BACKGROUND

A medical imaging system typically includes at least one medical modality that generates input pixel data representative of an image and a medical imager that forms a visible representation of the image based on the input pixel data. In a medical imaging system, the medical modality may include a diagnostic modality, such as a magnetic resonance (MR), computed tomography (CT), conventional radiography (X-ray), direct radiography (DR) or ultrasound imaging device. The input pixel data generated by the medical modality corresponds to a plurality of pixels in the original image and represents an optical density associated with the respective pixel. The medical imager processes the input pixel data to generate output image data. For example, in a continuous tone laser imager, the output image data represents exposure levels necessary for a scanning assembly to accurately reproduce the original image on an imaging element. The scanning laser exposes imaging media, such as a photosensitive film, to form the visible representation of the image. The output image data is used to modulate the intensity of the scanning laser while exposing the imaging media, thereby forming the visible representation of the original image. Other medical imagers use different imaging techniques to form output images such as direct thermal imaging, ablation imaging, dye transfer, ink jet, dye sublimation and thermal mass transfer.

In order to form an accurate reproduction of the input image, the medical imager applies a conversion mechanism, such as a transfer function or a lookup table, to convert the input pixel data to the output image data. A transfer function mathematically characterizes the relationship between the input pixel data and the output image data while a lookup table maps discrete input pixel data to output image data, thereby eliminating mathematical calculations. A user selects an appropriate conversion mechanism in order to enhance a desired characteristic of the input image such as contrast or density. In this fashion, the user selects a particular conversion mechanism that best highlights the important diagnostic information conveyed by the image. In other words, the conversion mechanism generates the output image data in a manner that accents the desired visual characteristic.

If the medical imager fails to produce the appearance characteristic desired by a system user, the diagnostic value of the resulting images can be impaired. The selection of appropriate conversion mechanisms is a time consuming task that requires considerable skill and effort. A service technician is often called upon to assist hospitals in selecting appropriate lookup tables and transfer functions based on the specific requirements of the hospital and the type of diagnostic images commonly produced by the hospital's medical modalities. Because of the continual demand for a hospital's medical imaging system, a lengthy service call to properly configure the medical imager may be a tremendous burden on the hospital's medical staff as well as the service technician. Accordingly, there is a need for an improved medical imaging system that is easily configured and maintained without interfering with hospital staff.

SUMMARY OF THE INVENTION

As explained in detail below, the present invention is directed to a method and system for remotely viewing and configuring output from a medical imaging device. In one aspect, the invention provides for more accurate display of medical images on a remote machine, thereby facilitating remote configuration of the medical imager. The more accurate display allows a service technician to more easily configure the medical imaging device without traveling to the hospital and burdening medical staff, including selecting conversion mechanisms best suited for highlighting various characteristics of the images.

In one embodiment, the invention is a medical imaging system including a medical modality for generating an input image having input pixel data. A medical imager is communicatively coupled to the medical modality and receives the input image from the medical modality and forms an output image on an imaging element based on the input pixel data of the input image. The medical imager includes an internal web server for generating an HTML document containing pixel data based on the input pixel data. A client machine is communicatively coupled to the medical imager and receives the HTML document from the medical imager for displaying the pixel data contained within the HTML document. The interface may be a conventional web browser or may be a custom interface for displaying the pixel data of the HTML document. In this manner, the input images received by the medical imager are accurately displayed by the remote client machine, thus allowing a service technician to easily configure the medical imager without traveling to the hospital and burdening medical staff.

The present invention facilitates the remote display of images that more accurately represent the output of a medical imager. For example, the web server of the medical imager may generate an HTML document containing output image data generated when the medical imager applies a conversion mechanism, such as a lookup table or transfer function, to the input pixel data. Alternatively, the web server may generates an HTML document containing the input image data such that the client machine applies a conversion mechanism to the contained pixel data of the HTML document for generating display image data for displaying on the interface. In this manner, image displayed by the client machine more accurately represents the output image formed by the medical imager. According to yet another feature, the HTML document does not contain pixel data but contains a hypertext link to the input images stored on the medical imager, thus allowing the service technician to selectively receive input images for remote viewing. Additionally, the HTML document may contain operating statistics such as a count of the number of imaging elements used by the medical imager.

According to another aspect of the invention, the medical imaging system may include a network such that the medical imager is connected to a second medical imager. The second medical imager generates a second HTML document and communicates the second HTML document to the client machine through the network. Thus, similar to the manner described above, a service technician is able to remotely view and configure output from a plurality of medical imagers.

In yet another embodiment, the invention is a method for configuring a medical imager having a plurality of stored conversion mechanisms. A web server of the medical imager is accessed via a web browser executing on a remote client machine communicatively coupled to the medical imager. Through the web browser, the medical imager is commanded to receive an input image having input pixel data and imaging information from a medical modality. The medical imager is then commanded to generate an HTML document containing the imaging information and pixel data representative of the input pixel data of the input image. The web browser receives the HTML document from the web server of the medical imager and displays the contained pixel data of the HTML document on the client machine according to the imaging information of the HTML document. One of the plurality of the conversion mechanisms of the medical imager is selected based on the displayed pixel data. Finally, the medical imager is commanded to apply the selected conversion mechanism to subsequent input images from the medical modality to form output images on an imaging element.

These and other features and advantages of the invention will become apparent from the following description of the preferred embodiments of the invention.

DETAILED DESCRIPTION

In the following detailed description, references are made to the accompanying drawings which illustrate specific embodiments in which the invention may be practiced. Electrical, mechanical and structural changes may be made to the embodiments without departing from the spirit and scope of the present invention. The following detailed description is, therefore, not to be taken in a limiting sense and the scope of the present invention is defined by the appended claims and their equivalents.

Figure 1:
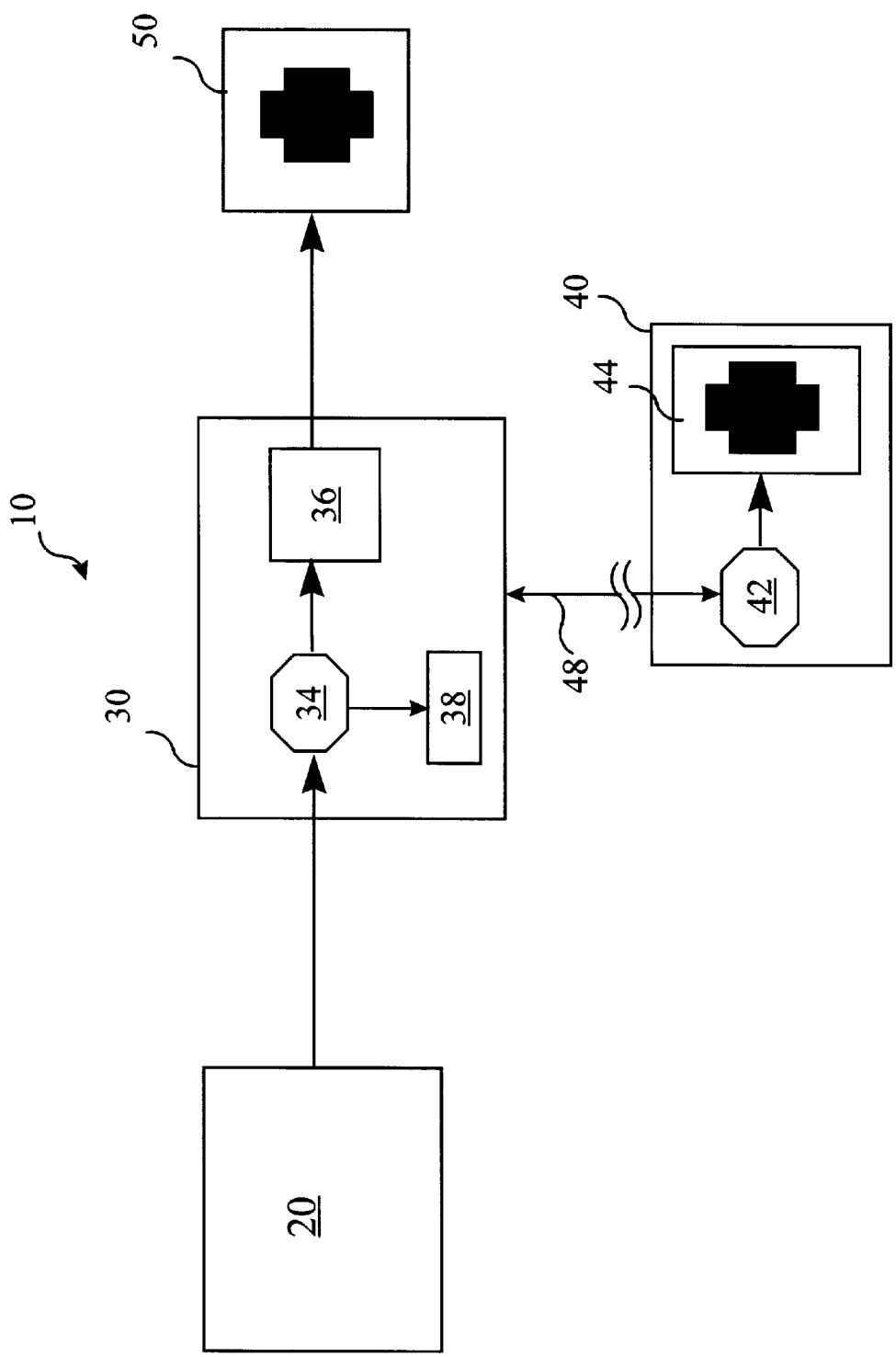
FIG. 1 is a block diagram illustrating one embodiment of a medical imaging system incorporating a method and system for remotely viewing and configuring output of a medical imager in accordance with the present invention.

FIG. 1 illustrates medical imaging system 10 in block diagram form. Medical imaging system 10 includes medical modality 20, medical imager 30, client machine 40 and imaging element 50. Medical modality 20 generates an input image having input pixel data and may be any suitable diagnostic modality such as a magnetic resonance (MR), computed tomography (CT), digital radiography (DR) or ultrasound imaging device. Each of the input pixel data corresponds to one of a plurality of pixels in the original input image, and represents an optical density associated with the respective pixel. Medical modality 20 communicates the generated input image to medical imager 30 for forming a representative output image on imaging element 50. Typically, medical modality 20 communicates the input pixel data of the input image as well as imaging information that specify characteristics of the modality or operations to be performed by medical imager 30 on the communicated input pixel data.

Medical imager 30 is communicatively coupled to medical modality 20 and may be any medical imaging device suitable for receiving the input image from medical modality 20 and forming an output image on imaging element 50. In one embodiment medical imager 30 is a continuous tone laser imager. Furthermore, imaging element 50 may be photographic such that medical imager 30 includes a processor station (not shown) for chemical processing and developing of the output image formed on imaging element 50. In another embodiment, imaging element 50 may be photothermographic which can be thermally processed and need not be chemically processed.

Prior to forming the output image on imaging element 50, controller 34 of medical imager 30 performs a number of operations on the input pixel data according to the imaging information received from medical modality 20. For example, medical imager 30 may rotate or magnify the input pixel data. Additionally, controller 34 applies at least one of a plurality of conversion mechanisms to convert the input pixel data to output image data for forming on imaging element 50. Typically, controller 34 applies a user selected conversion mechanism in order to achieve a desired appearance characteristic such as contrast or density. In this manner, the conversion mechanism generates the output image data necessary to produce the appearance characteristic desired by the user. For example, in one embodiment controller 34 applies a lookup table to convert the received input pixel data to output image data. In another embodiment, controller 34 applies a transfer function to the input pixel data in order to calculate a corresponding output image data.

After generating output image data from the input pixel data, controller 34 commands medical imager 30 such that radiation source 36 forms a representation of the input image on imaging element 50. In one embodiment, radiation source 36 comprises a laser diode scan module for emitting a suitable beam of radiation. Other imaging processes are also suitable for the present invention including direct thermal imaging, ablation imaging, dye transfer, ink jet, dye sublimation and thermal mass transfer. Furthermore, controller 34 represents any logic circuit suitable for device control. For example, controller 34 may be an embedded microprocessor having RAM for data manipulation and general program execution.

In conventional imaging systems, a user typically selects an appropriate conversion mechanism for the medical imager in order to produce an output image having high diagnostic value. As discussed above, selection of the appropriate conversion mechanism is based in part on characteristics of input images and the medical modalities. The selection may requires great time and effort from hospital personnel and service technicians. For these reasons, according to one feature of the present invention a service technician can configure medical imager 30 by accessing medical imager 30 from client machine 40. More specifically, a service technician can perform a variety of configuration and maintenance operations on medical imager 30 from client machine 40 via communications link 48. In one embodiment, client machine 40 is remote from the hospital and communications link 48 allows the service technician to easily configure medical imager 30 using a modem or other communications device. In another embodiment, medical imager 30 and client machine 40 are co-located within a hospital and communications link 48 directly connects the two devices.

Client machine 40 is a computer configured for executing suitable communication protocols, such as the Transmission Control Protocol/Internet Protocol (TCP/IP) and the File Transport Protocol (FTP), over communications link 48. Upon accessing medical imager 30 from client modality 40, the service technician commands web server 38 of medical imager 30 to generate an HTML document based on the input image received from medical modality 20. Web server 38 may generate the HTML document in one of several way. In one embodiment, web server 38 generates an HTML document containing the input pixel data as well as the imaging information received from medical modality 20. In another embodiment, controller 34 applies imaging operations and selected conversion mechanisms to the input pixel data based on the imaging information of the input image such that web server 38 generates an HTML document containing output image data. This embodiment is beneficial because client machine 40 need not apply imaging operations to the pixel data contained within the HTML document prior to displaying the pixel data on interface 44. In yet another embodiment, web server 38 generates an HTML document containing hypertext links to the input images stored by medical imager 30. This embodiment is beneficial in that a service technician can select the images to be remotely viewed, thereby limiting the amount of communicated pixel data.

Upon receiving the HTML document generated by web server 38, controller 42 of client machine 40 manipulates the contained pixel data according to any imaging operations specified within the HTML document. For example, controller 42 applies any conversion mechanisms communicated by the HTML document, thereby converting the contained pixel data to display image data for displaying on interface 44. In one embodiment, client machine 40 maintains a plurality of conversion mechanisms and selects an appropriate mechanisms based on the imaging information contained within the HTML document.

By application of a conversion mechanism to the contained pixel data similar to the mechanism applied by medical imager 30, the image displayed on interface 44 more accurately represents the output image formed on imaging element 50. Because of the invention more accurately displays medical images, the service technician can easily select conversion mechanisms best suited for the specific characteristics of the images produced by the hospital's medical modalities without traveling to the hospital and involving medical staff.

In addition to pixel data and imaging information, web server 38 may generate the HTML document to include various operating statistics. For example, in one embodiment processor 34 maintains a count of the number of imaging elements used by medical imager 30 and communicates the count via the generated HTML document. Based on the operating statistics, client machine 40 can be used to remotely determine whether a service call is needed or whether new supplies should be sent to the hospital.

Figure 2:
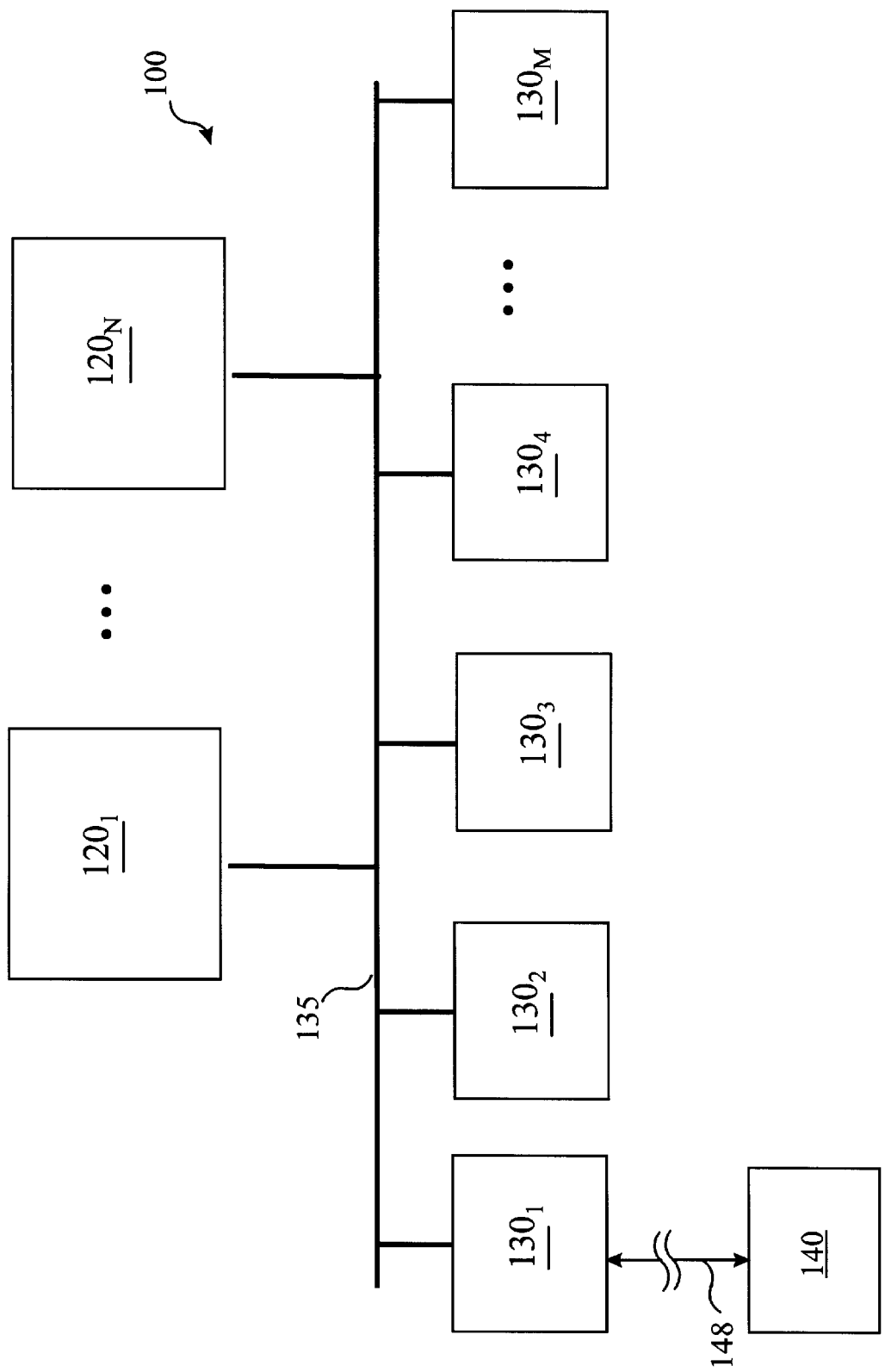
FIG. 2 is a block diagram illustrating one embodiment of a medical imaging system having a plurality of networked medical imagers and incorporating the present invention.

FIG. 2 is a block diagram illustrating one embodiment of a medical imaging system 100 having a plurality of M medical imagers 130 and a plurality of N medical modalities 120 interconnected by network 135. The networked configuration allows images produced by any medical modality 120 to be routed to any available medical imager 130. As in imaging system 10 of FIG. 1, medical modalities 120 communicate input images to medical imagers 130 for forming on imaging elements. Unlike imaging system 10, medical modalities 120 communicates the input images over network 135 using a suitable network protocol. For example, in one embodiment, network 135 is an Ethernet network using twisted pair, coaxial cable or fiber-optic connection. Furthermore, medical imagers 130 and medical modalities 120 implement a common communications protocol. In one embodiment, medical modalities 120 exchange data and information with medical imagers 130 using a data communications protocol developed by the American College of Radiology (ACR) and the National Electrical Manufacturers Association (NEMA) known as the DICOM protocol. Typically, the protocol may be implemented using a TCP/IP connection between medical modalities 120 and medical imager 130 over network 135.

Configuration of each medical imager 130 is complicated due to the plurality of medical modalities 120. Each medical modality may be of different type, such as magnetic resonance (MR), computed tomography (CT), digital radiography (DR) or ultrasound. Each medical modality 120 may, therefore, have different imaging characteristics and features. Each medical imager 130 may need to apply different conversion mechanisms to input images received from different medical modalities 130 in order to form output images having high diagnostic value. The potential for a wide variety of medical modalities 120 further increases the time and effort required by hospital personnel and service technicians to configure medical imagers 130. Thus, according to one feature of the present invention, a service technician can configure each medical imager 130 by first accessing medical imager $130_1$ from client machine 140. In this manner, a service technician can perform a variety of configuration and maintenance operations on each medical imager 130 via communications link 148 and network 135.

Similar to client machine 40 of FIG. 1, client machine 140 of FIG. 2 is a computer configured for executing suitable communication protocols, such as TCP/IP and FTP, over communications link 148. Upon accessing medical imager $130_1$ from client machine 140, the service technician may initiate configuration of medical imager $130_1$ by commanding medical imager $130_1$ to request an input image from one of the plurality of medical modalities 120. Upon receiving the request the selected medical modality 120 will produce a test image. Alternatively, hospital personnel or a service technician can manually initiate the generation of an input image by one of the medical modalities 120. The service technician commands a web server (not shown) of medical imager $130_1$ to generate an HTML document based on the test input image received from the selected medical modality 120. As yet another alternative, the service technician may command the web server of medical imager $130_1$ to generate the HTML document based on actual diagnostic input images received from a medical modality 120. Upon receiving the HTML document generated by the web server of medical imager $130_1$, client machine 140 manipulates the contained pixel data according to any imaging operations specified within the HTML document, thereby converting the contained pixel data to display image data. By application of imaging operations, such as conversion mechanism, the image displayed by client machine 140 more accurately represents the output image formed by medical imager $130_1$. In this manner, client machine 140 allows a service technician to display an image that closely approximates the output image formed by medical imager $130_1$.

Because each medical imager 130 is connected via network 135 and includes an internal web server, the service technician is able to remotely access each of the plurality of medical imagers 130 from client machine 148. In other words, by accessing medical imager $130_1$ via communications link 148, client machine 140 is able to communicate with any medical imager 130 connected to network 135. The service technician is able to communicate with the internal web server of each medical imager 130 and configure each medical imager 130 according to the process described above. In this fashion the invention facilitates remote viewing of the medical images produced by a plurality of medical modalities. The accuracy and convenience of the present invention allow a service technician to select conversion mechanisms best suited for the each medical modality used by the hospital without traveling to the hospital. Furthermore, based on communicated statistics as described above, the service technician can remotely determine whether a service call is needed for any of the medical imagers or whether new supplies should be sent to the hospital. This application is intended to cover any adaptations or variations of the present invention. It is manifestly intended that this invention be limited only by the claims and equivalents thereof.

I claim:

1. A medical imaging system comprising:
    a medical modality for generating an input image having input pixel data and imaging information;
    a medical imager communicatively coupled to the medical modality for receiving the input image from the medical modality, wherein the medical imager selects a conversion mechanism in order to enhance a desired characteristic of the input image including one of contrast or density from a first plurality of stored conversion mechanisms based on the imaging information and applies the selected conversion mechanism to the input pixel data to generate output pixel data for forming an output image on an imaging element, and further wherein the medical imager includes a web server for generating an HTML document containing the imaging information and pixel data representative of the input pixel data; and
    a client machine communicatively coupled to the medical imager for receiving the HTML document form the medical imager, wherein the client machine includes an interface for displaying the pixel data contained within the HTML document.

2. The system of claim 1, wherein the interface is a web browser.

3. The system of claim 1, wherein the pixel data of the HTML document is a copy of the output image data.

4. The system of claim 1, wherein the pixel data of the HTML document is a copy of the input image data.

5. The system of claim 4, wherein the client machine includes a second plurality of stored conversion mechanisms, and further wherein the client machine selects a conversion mechanism of the second plurality of conversion mechanisms based on the image information of the HTML and applies the selected conversion mechanism of the second plurality of conversion mechanisms to the contained pixel data of the HTML document to generate display image data for displaying on the interface.

6. The system of claim 5, wherein the conversion mechanism of the medical imager and the conversion mechanism of the client machine each include at least one lookup table.

7. The system of claim 5, wherein the conversion mechanism of the medical imager and the conversion mechanism of the client machine each include at least one transfer function.

8. The system of claim 4, wherein the web server communicates the selected conversion mechanism of the first plurality of conversion mechanisms to the client machine, and further wherein the client machine applies the selected conversion mechanism to the contained pixel data for generating display image data for displaying on the interface.

9. The system of claim 1, wherein the HTML document contains operating statistics of the medical imager including at least a count of used imaging elements.

10. The system of claim 1, wherein the medical imager includes a modem for communicating with the client machine.

11. The system of claim 1, wherein the client machine and the medical imager communicate using the Transmission Control Protocol (TCP) and the Internet Protocol (IP).

12. The system of claim 1, wherein the HTML document received by the client machine contains a hypertext link for receiving the contained pixel data from the medical image.

13. The system of claim 1, wherein the medical imager is connected to a network having at least a second medical imager, and further wherein the second medical imager generates a second HTML document and communicates the second HTML document to the client machine through the network.

14. A medical imaging system comprising:
    a plurality of medical modalities for generating input images having input pixel data;
    a plurality of medical imagers for forming output images based on the input pixel data of the input images, wherein the medical imagers and the medical modalities are interconnected by a network for communicating the input images form the medical modalities to the medical imagers, wherein each medical imager applies a conversion mechanism in order to enhance a desired characteristic of the input image, including one of contrast or density to the input pixel data to generate output image data for forming on the image element, and further wherein the pixel data of the HTML document is a copy of the output image data.

15. The system of claim 14, wherein the interface is a web browser.

16. The system of claim 14, wherein the pixel data of the HTML document is a copy of the input image data.

17. The system of claim 16, wherein the client machine stores a plurality of conversion mechanisms and applies at least one conversion mechanism to the contained pixel data of the HTML document to generate display image data for displaying on the interface.

18. The system of claim 16, wherein the web server communicates a conversion mechanism to the client machine, and further wherein the client machine applies the conversion mechanism to the contained pixel data for generating display image data for displaying on the interface.

19. A method for configuring a medical imager having a plurality of stored conversion mechanisms in order to enhance a desired characteristic of the input image including one of contrast or density comprising the steps of;
    accessing a web server of the medical imager with a web browser executing on a remote client machine communicatively coupled to the medical imager;
    commanding the medical imager to receive an input image having input pixel data and image information from a medical modality;
    commanding the medical imager to generate an HTML document containing the imaging information and pixel data representative of the input pixel data of the input image;
    receiving the HTML document from the web server of the medical imager;
    selecting one of the plurality of the conversion mechanisms of the medical imager based on the pixel data and the imaging information of the HTML document; and
    commanding the medical imager to apply the selected conversion mechanism to subsequent input images from the medical modality to form output images on an imaging element.

20. The method of claim 19, wherein the selecting step includes the step of displaying the contained pixel data of the HTML document on the client machine according to the imaging information of the HTML document.

* * * * *